(12) United States Patent
Jones et al.

(10) Patent No.: US 8,538,112 B2
(45) Date of Patent: Sep. 17, 2013

(54) ADAPTIVE FRAMING FOR DYNAMIC CARDIAC PET STUDIES

(75) Inventors: Judson P. Jones, Knoxville, TN (US); Michael E. Casey, Louisville, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 422 days.

(21) Appl. No.: 13/023,602

(22) Filed: Feb. 9, 2011

(65) Prior Publication Data

US 2012/0201471 A1    Aug. 9, 2012

(51) Int. Cl.
*G06K 9/46* (2006.01)
*G06K 9/00* (2006.01)
*A61B 5/05* (2006.01)

(52) U.S. Cl.
USPC .................... 382/131; 382/207; 600/410

(58) Field of Classification Search
USPC ................. 382/128–132; 600/410
See application file for complete search history.

(56) References Cited

U.S. PATENT DOCUMENTS

2001/0039377 A1* 11/2001 Maier et al. ............. 600/410
2009/0316972 A1* 12/2009 Borenstein et al. ........... 382/131

OTHER PUBLICATIONS

Lortie et al, "Quantification of Myocardial Blood Flow with 82Rb Dynamic PET Imaging", Eur. J. Nucl. Med. Mol. Imaging, (2007) 34:1765-1774).*
Lortie et al "Quantification of Myocardial Blood Flow with 82Rb Dynamic PET Imaging", Eur. J. Nucl. Med. Mol. Imaging, (2007) 34:1765-1774).*
Lorte, Quantification of Myocardial Blood Flow with 82Rb Dynamic PET Imaging, Eur. J. Nucl. Med. Mol. Imaging (2007) 34: 1765-1774.
El Fakhri, Absolute Quantitation of Regional Myocardial Blood Flow (MFB) Using Rb-82 PET: Experimental Validation Using Microspheres, J. Nucl. Med. 2007, 48 (Supplement 2) 54P.

* cited by examiner

*Primary Examiner* — Amara Abdi
(74) *Attorney, Agent, or Firm* — Peter Kendall

(57) ABSTRACT

Methods and computer-readable mediums are provided. In one embodiment, the method acquires patient data. The peak value in the patient data is determined. The patient data is divided into two data segments (i.e., one data segment representing the data before the peak value occurs and a second data segment representing the patient data after the peak occurs). The slopes of the first and second data segments are calculated. Thereafter the slopes are used to determine an appropriate adaptive framing protocol. A number of frames and duration of each frame in the adaptive framing protocol can be calculated or the adaptive framing protocol can be selected from a plurality of framing protocols. Embodiments of the invention also include computer-readable mediums that contain features similar to the features in the above described method.

16 Claims, 6 Drawing Sheets

ADAPTIVE FRAMING FOR DYNAMIC CARDIAC PET STUDIES

BACKGROUND

1. Field of the Invention

Embodiments of the present invention generally relate to nuclear medicine, and systems for obtaining images of a patient's body organs of interest. In particular, the present invention relates to a novel method and system for utilizing an adaptive framing protocol in medical imaging.

2. Description of the Related Art

Heart disease is very common. The heart can be evaluated for large vessel and small vessel disease. One by-product of small vessel heart disease is poor heart oxygenation.

Nuclear medicine is a unique medical specialty wherein radiation is used to acquire images that show the function and anatomy of organs, bones and/or tissues of the body. Radiopharmaceuticals are introduced into the body, either by injection or ingestion, and are attracted to specific organs, bones and/or tissues of interest. For example, the radiopharmaceutical (e.g., rubidium) is injected into the bloodstream.

The radiopharmaceutical produces gamma photon emissions that emanate from the body. One or more detectors are used to detect the emitted gamma photons and the information collected from the detector(s) is processed to calculate the position of origin of the emitted photon from the source (i.e., the body organ or tissue under study). The accumulation of a large number of emitted gamma positions allows an image of the organ or tissue under study to be displayed.

How fast the radiopharmaceutical is taken in by the heart indicates how quickly the heart is being oxygenated and also indicates how healthy the small micro-vessels are in the heart. The rate of absorption of the radiopharmaceutical is determined by comparing the amount of radiopharmaceutical at one time with the amount at another time.

To calculate the rate of absorption, measurements are taken at various times. Data is acquired for each patient under "rest" and "stress" conditions. Stress is usually induced through either some form of exertion (e.g., walking or running on a treadmill) or by injection of a chemical which increases the heart rate. The ratio between stress and rest in a healthy heart is about a factor of 4 and in a diseased heart the stress/rest ratio is about a factor of 1.2.

In PET studies of cardiac function, emission data are typically collected in list mode. The list is then divided into a predetermined temporal sequence of frames (using a framing protocol), an image is reconstructed from the data in each frame, and the sequence of reconstructed images analyzed for evidence of disease.

To date, framing protocols have universally been fixed for every patient. Clinicians choose some invariant sequence of framing times, which never changes. These fixed framing protocols are the same within each clinic.

For example, Lorte, *Quantification of Myocardial Blood Flow with 82Rb Dynamic PET Imaging*, Eur. J. Nucl. Med. Mol. Imaging (2007) 34: 1765-1774, ("Lortie et al.") analyzes all patient data using a framing protocol that consists of 17 frames organized as 12*10 s+2*30 s+1×60 s+1×120 s+1× 240 s; and El Fakhri, *Absolute Quantitation of Regional Myocardial Blood Flow (MFB) Using RB-82 PET: Experimental Validation Using Microspheres*, J. Nucl. Med. 2007, 48 (Supplement 2) 54P, ("El Fakhri et al.") analyzes all patient data using a framing protocol that consists of 34 frames organized as 24*5 s+6*10 s+4*20 s. In some studies, the first frame is started on a signal derived from the data, but in all studies the timing of the frames does not depend on any features of the data.

After image reconstruction, the amount of radioactivity in the heart can be measured.

One way to estimate dynamic physiological parameters from quantitative reconstructed images is given by Lortie et al., using a one-compartment model:

$$C_m(t)=K_1 e^{-k_2 t} * C_a(t) \qquad \text{Equation (1)}$$

where $C_a(t)$ and $C_m(t)$ are the measured concentrations of the radiotracer in the arterial blood and the tissue of interest, respectively. $K_1$ is a measure of how quickly the radiotracer flows into the tissue of interest and $k_2$ represents how quickly it flows out. To estimate the model parameters $K_1$ and $k_2$, least squared error minimization can be used, with each frame assigned a weight proportional to its duration in time.

The prior art analyzes small vessel disease using a fixed framing protocol which often leads to an excessive number of frames used in the analysis.

Therefore, there exists a need in the art for a protocol which is adapted for each individual patient to minimize the number of frames used in the analysis of the medical images.

SUMMARY

These and other deficiencies of the prior art are addressed by embodiments of the present invention, for obtaining images of a patient's body organs of interest. In particular, the present invention relates to a novel method and system for utilizing an adaptive framing protocol in medical imaging. In one embodiment, the method acquires patient data. The peak value in the patient data is determined. The patient data is divided into two data segments (i.e., one data segment representing the data before the peak value occurs and a second data segment representing the patient data after the peak occurs). The slopes of the first and second data segments are calculated. Thereafter the slopes are used to determine an appropriate adaptive framing protocol. A number of frames and duration of each frame in the adaptive framing protocol can be calculated or the adaptive framing protocol can be selected from a plurality of framing protocols. Embodiments of the invention also include computer-readable mediums that contain features similar to the features in the above described method.

Other embodiments are also provided in which a computer-readable medium performs similar features recited by the above method.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

To facilitate understanding, identical reference numerals have been used, wherever possible, to designate identical elements that are common to the figures.

DETAILED DESCRIPTION

In the following description, numerous specific details are set forth to provide a more thorough understanding of the invention. As will be apparent to those skilled in the art, however, various changes using different configurations may be made without departing from the scope of the invention. In other instances, well-known features have not been described in order to avoid obscuring the invention. Thus, the invention is not considered limited to the particular illustrative embodiments shown in the specification and all such alternate embodiments are intended to be included in the scope of the appended claims.

Aspects of this disclosure are described herein with respect to applying an adaptive framing protocol in PET systems. However, the description provided herein is not intended in any way to limit the invention to PET systems. Aspects of the material disclosed herein may be utilized in other imaging technologies (e.g., SPECT systems, etc.).

Although aspects of this disclosure are described herein with respect to blood flow through a heart, those descriptions are for exemplary purposes only and not intended in any way to limit the scope of the material disclosed herein. For example, the material disclosed herein may be used to examine blood flow through other organs/limbs/tissue (e.g., a toe, brain, etc.).

Some guidelines in selecting a framing protocol are (1) during initial phase of acquisition, when the data are changing rapidly, to divide the data into a large number of short flames, to capture the dynamics; (2) during a later phase of acquisition, when the data are changing slowly (when compared to the initial phase), to divide the data into a small number of long frames, to maximize noise performance; (3) to choose a framing protocol which behaves properly given the range dynamical behavior observed in all clinical data sets (i.e., from all patients); and (4) to minimize the overall number of frames so as to reduce the computational burden, and the time, needed by image reconstruction and analysis.

Figure 1:
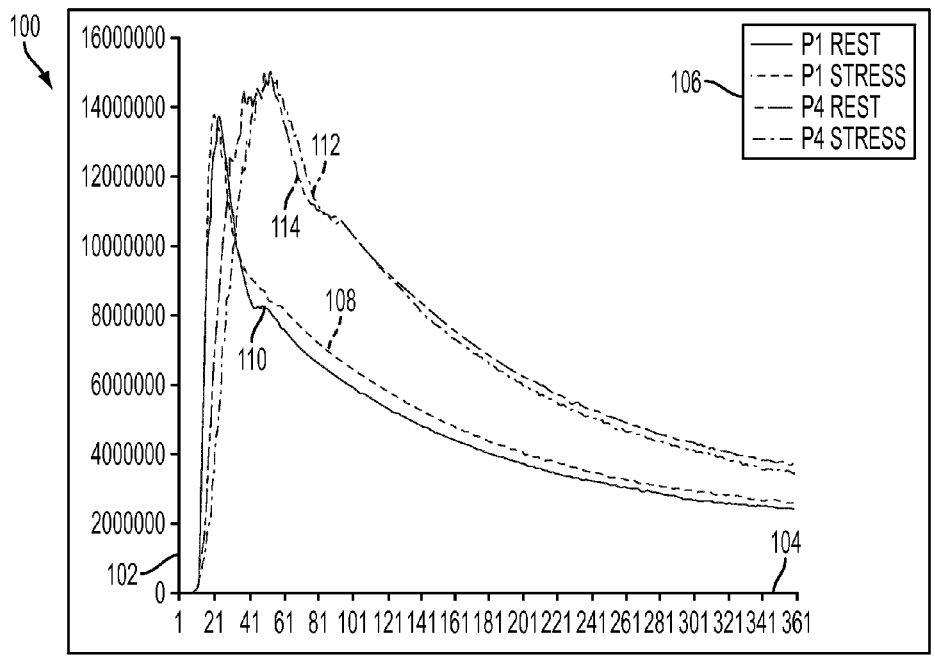
FIG. 1 depicts a graph in accordance with the prior art.

FIG. 1 (prior art) depicts a graph 100 of cardiac rubidium studies of two patients. Specifically, the graph 100 includes a "Y" axis 102 delineating a number of radioactive decay events and an "X" axis 104 delineating time in seconds. The graph 100 includes two cardiac rubidium plots (P1 Rest 110 and P1 Stress 108) for patient P1, and two cardiac rubidium plots (P4 Rest 114 and P4 Stress 112) for patient P4. The graph 100 also includes a legend 106 identifying each of the plots ("P1 Rest," "P2 Stress," "P4 Rest," and "P4 Stress") in graph 100. Note that the P1 Rest 110 and P1 Stress 108 reach their peak before P4 Rest 114 and P4 Stress 112. In other words, the level of radiotracer increases more rapidly for P1 than for P4.

Figure 2:
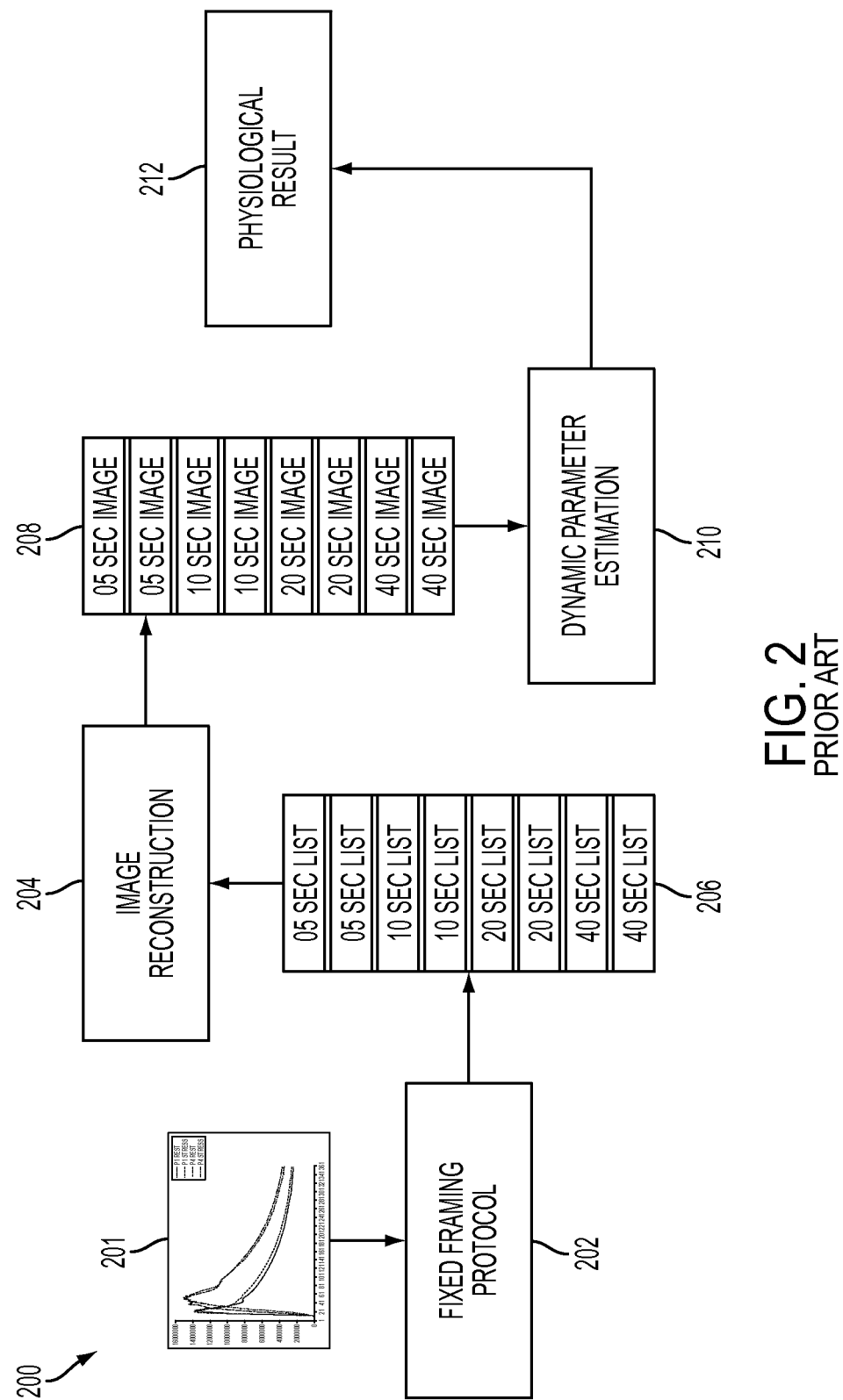
FIG. 2 depicts a data flow diagram in accordance with the prior art.

FIG. 2 depicts a data flow diagram 200 in accordance with a fixed framing protocol of the prior art. Specifically, the data flow diagram 200 includes PET event data 201 acquired from a patient. For illustrative purposes, the PET event data is the data (i.e., the plots P1 Rest, P1 Stress, P4 Rest, and P4 Stress) depicted in graph 100. Fixed framing protocol 202 is a fixed framing protocol utilized by a clinic for all patients examined by the clinic. In this example of the prior art, the fixed framing protocol 202 includes eight segments (two 5 sec, two 10 sec, two 20 sec, and two 40 sec segments) depicted as look-up table 206. The event data 201 is divided into eight list segments and mapped to a fixed framing protocol algorithm 202. The length of each segment is predetermined in advance regardless of the dynamic data of an individual patient. The data in look-up table 206 is used by an image reconstruction module 204. These list segments are then individually reconstructed as two 5 sec images, two 10 sec images, two 20 sec images, and two 40 sec images, yielding a fixed number of images 208. Quantities extracted from the image sequence are then used to perform dynamic parameter estimation (e.g., using Equation (1)), yielding some physiological result 212.

Figure 3:
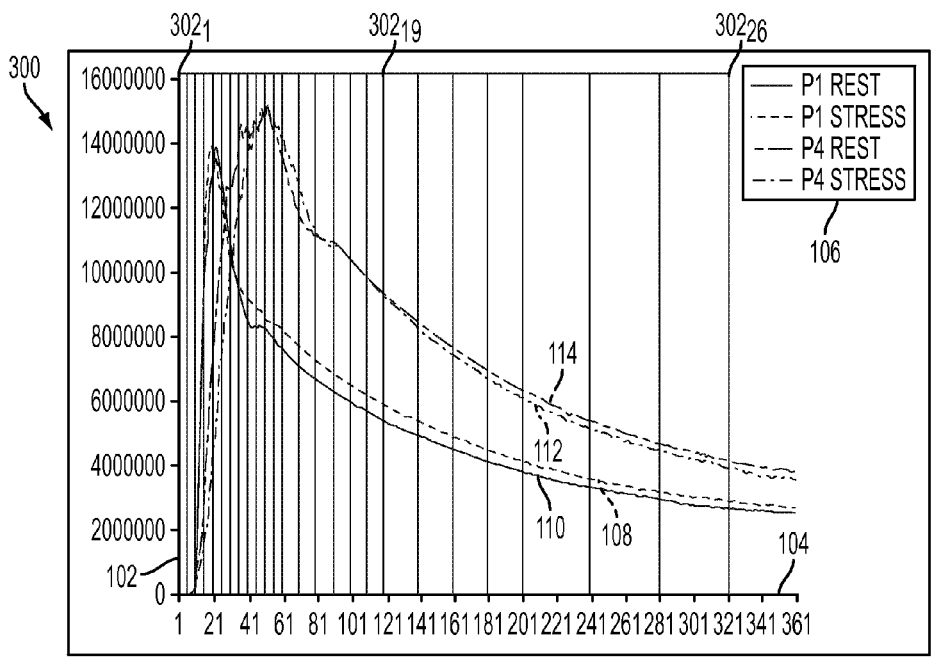
FIG. 3 depicts a fixed frame protocol in accordance with the prior art.

FIG. 3 depicts a fixed frame protocol 300 applied to graph 100 in accordance with the prior art. Specifically, FIG. 3 includes the "Y" axis 102 delineating the number of radioactive decay events and the "X" axis 104 delineating time in seconds. FIG. 3 also includes the two cardiac rubidium plots (P1 Rest 110 and P1 Stress 108) for patient P1, and the two cardiac rubidium plots (P4 Rest 114 and P4 Stress 112) for patient P4. In addition, the legend 106 identifying each of the plots ("P1 Rest," "P2 Stress," "P4 Rest," and "P4 Stress") is depicted.

This protocol is a fixed framing protocol and consists of 26 frames (i.e., twelve 5 sec, six 10 sec, four 20 sec, and four 40 sec frames). In this diagram the vertical lines $302_1, 302_{19}, \ldots, 302_{26}$ (collectively vertical lines 302) indicate the segments in time for subsequent analysis. The plots of patient P1 peaks prior to the plots of patient P4. However, the fixed framing protocol doesn't take into account the faster increase in rubidium levels of P1 relative to P4.

In general, the fixed framing leads to an excessive number of frames (before and after a peak occurs), since the high-frequency part at the beginning of the fixed protocol must be long enough to capture the activity peak in all studies, regardless of how late the peak occurs.

Aspects disclosed herein tailor the framing protocol to adapt to the observed peak in each individual data set, by performing a fast, preliminary analysis of the data while it is still in list mode. The adaptive framing protocol samples at the appropriate frequency around peak activity and at lower frequency after the peak. As a result, the number of frames utilized by this method is significantly less than the number of frames required by the fixed framing method, with little or no loss of dynamic resolution.

Figure 4:
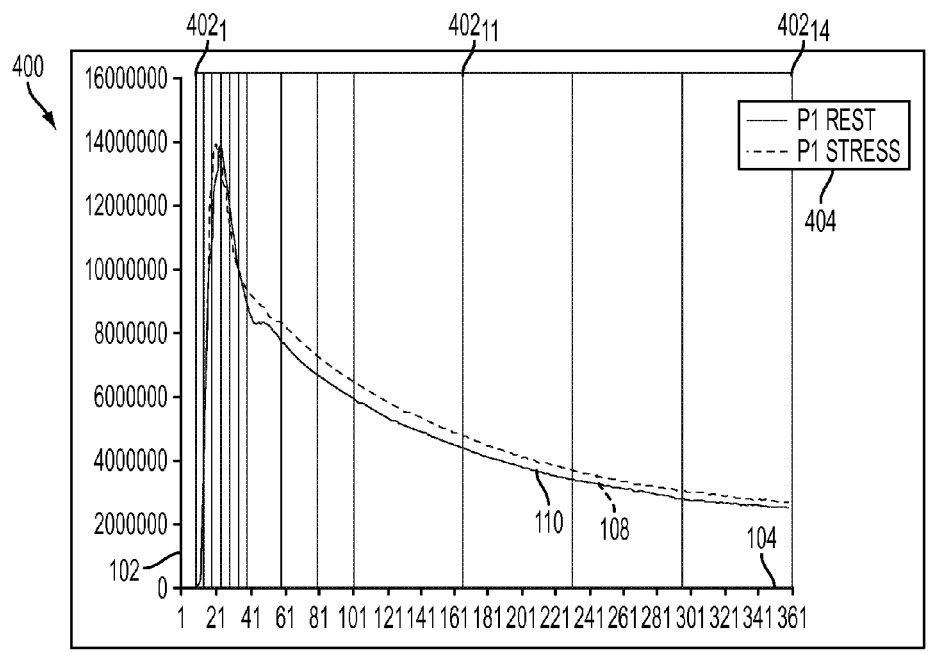
FIG. 4 depicts a graph in accordance with aspects disclosed herein.

FIG. 4 depicts a graph 400 in accordance with aspects disclosed herein. Specifically, FIG. 4 includes the "Y" axis 102 delineating the number of radioactive decay events and the "X" axis 104 delineating time in seconds. FIG. 4 also includes the two cardiac rubidium plots (P1 Rest 110 and Pt Stress 108) for patient P1. In addition, a legend 404 identifying both plots for P1 is depicted. FIG. 4 illustrates the results of an adaptive framing protocol applied to P1 Rest 110 and P1 Stress 108. The data, while still in list mode, is analyzed (using e.g., a polynomial approximation) to determine when a peak value occurs. As a result, short sequences are applied before the determined peak value and longer sequences are applied after the determined peak.

In FIG. 4, the adaptive protocol includes fourteen frames $((402_1, \ldots, 402_{11}, \ldots, \text{and } 402_{14})$ collectively frames 402). Because P1 Rest 110 and P1 Stress 108 peak earlier than P4

Rest 114 and P4 Stress 112 shorter frames can be applied to P1 Rest 110 and P1 Stress 108 up to the determined peak and longer sequences can be applied after the determined peak. In the sharply peaked case of patient P1, a smaller number (relative to patient P4) of high frequency frames are used prior to peak.

Figure 5:
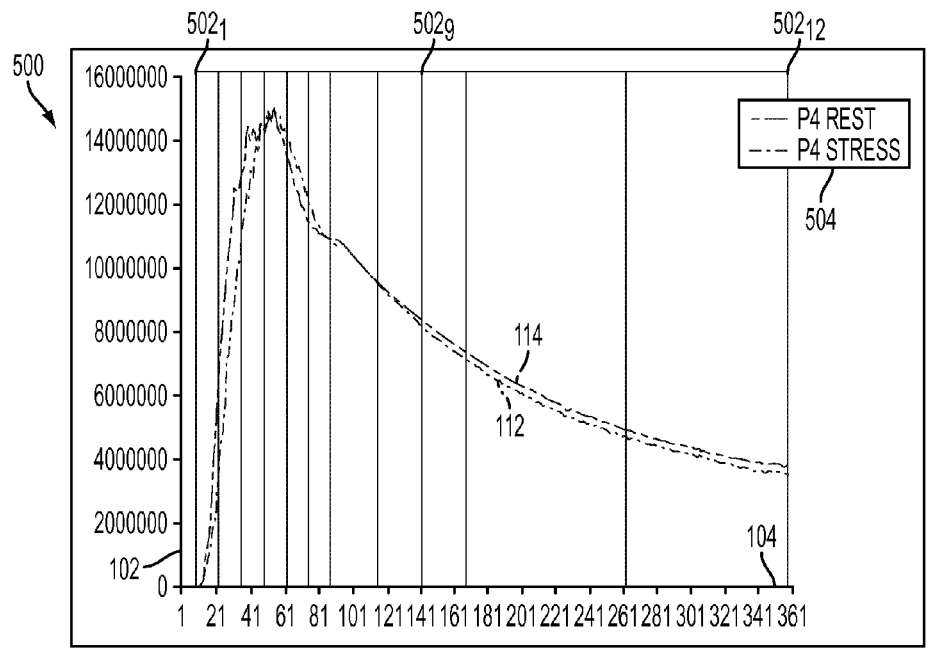
FIG. 5 depicts another graph in accordance with aspects disclosed herein.

FIG. 5 depicts another graph 500 in accordance with aspects disclosed herein. Specifically, FIG. 5 includes the "Y" axis 102 delineating the number of radioactive decay events and the "X" axis 104 delineating time in seconds. FIG. 5 also includes the two cardiac rubidium plots (P4 Rest 114 and P4 Stress 112) for patient P4. In addition, a legend 504 identifying both plots for P4 is depicted.

FIG. 5 illustrates the results of an adaptive framing protocol applied to P4 Rest 114 and P4 Stress 112. The data for P4, while still in list mode, is analyzed (using e.g., a polynomial approximation) to determine when a peak value occurs. The plots for patient P4 peak slower (than patient P1) which allows lower frequency frames (i.e., fewer frames) before peak occurs.

In FIG. 5, the adaptive protocol includes twelve frames (($502_1$, ..., $502_9$, ..., and $502_{12}$) collectively frames 502). Because P1 Rest 110 and P1 Stress 108 peak earlier than P4 Rest 114 and P4 Stress 112 shorted frames can be applied to P1 Rest 110 and P1 Stress 108 up to the determined peak and longer sequences can be applied after the determined peak. Juxtaposition (not shown) of FIGS. 4 and 5 shows the differences between the framing protocols (i.e., frames 402 and 502) utilized to analyze patients P1 and P4 respectively.

Figure 6:
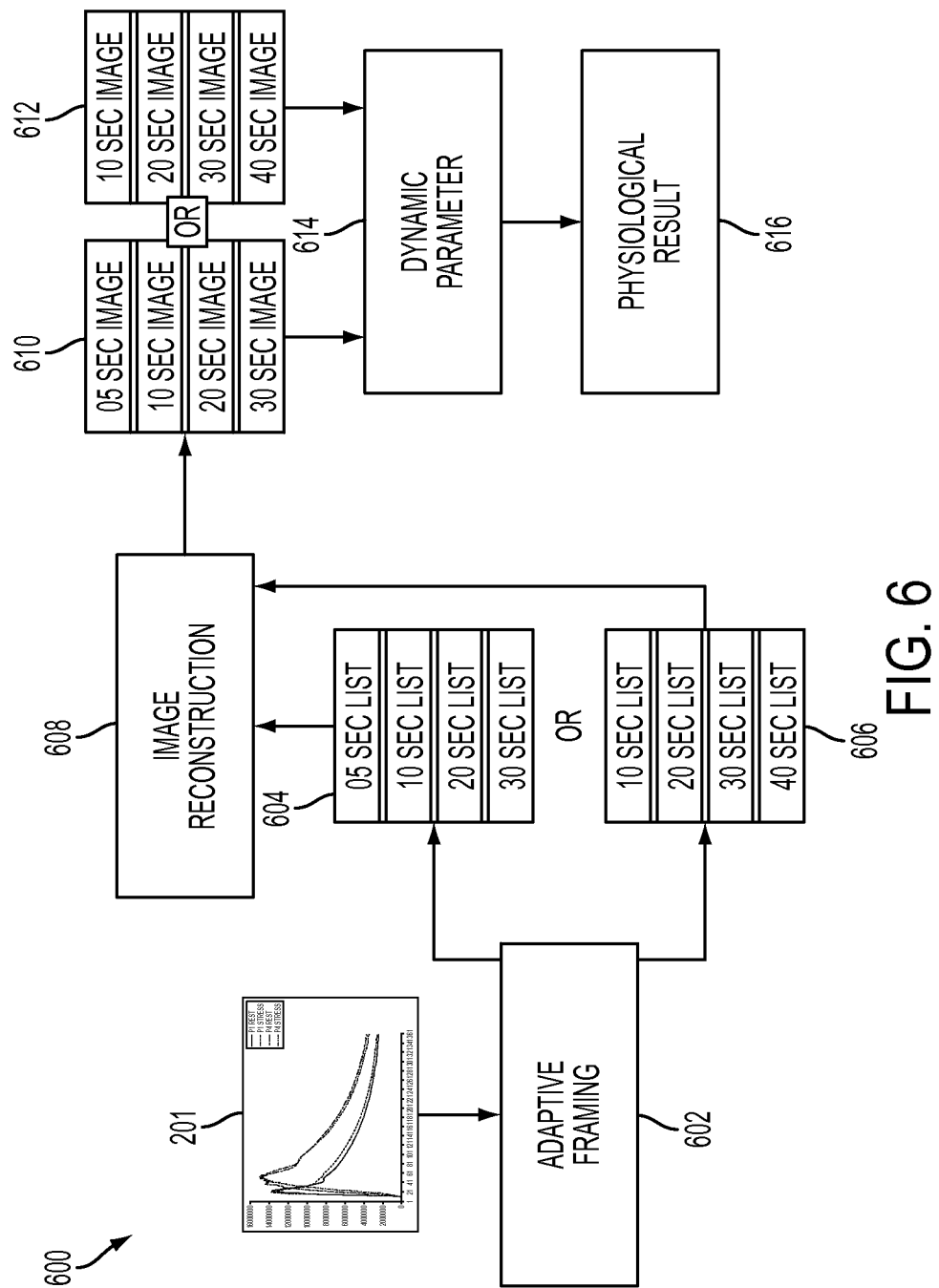
FIG. 6 depicts an embodiment of a data flow diagram in accordance with aspects disclosed herein.

FIG. 6 depicts a data flow diagram 600 in accordance with aspects disclosed herein. Specifically, the data flow diagram 600 includes PET event data 201 acquired from all of the patients. For illustrative purposes, the PET event data is the data (i.e., the plots P1 Rest, P1 Stress, P4 Rest, and P4 Stress) depicted in graph 100. An adaptive framing module 602 is separately applied to the data for each patient (i.e., applied to patient P1 and P4 separately).

Illustratively, the adaptive framing module 602 is depicted as being one of two different framing protocols (framing protocols 604 and 606). However, that depiction is not intended in any way to limit the scope of the invention. For example, the adaptive framing module 602 may contain more than two framing protocols.

Framing protocol 604 includes four frames (four 5 sec, one 10 sec, one 20 sec, and one 30 sec frames) and framing protocol 606 includes four frames (one 10 sec one 20 sec, one 30 sec, and one 40 sec frames). The number of frames is for illustrative purposes only and is used to depict that there is a difference between framing protocols 604 and 606.

After analyzing a patient's data, a determination is made which framing protocol is the most appropriate framing protocol to utilize for the patient. After the determination is made which of the framing protocols is the most appropriate the data can be subsequently analyzed by an image reconstruction module 608. These list segments are then individually reconstructed into image lists (in this example depicts as one of two image lists 610 and 612 corresponding to the adaptive framing protocol previously selected). Quantities extracted from the image sequence are then used to perform dynamic parameter estimation by the dynamic parameter module 614, yielding some physiological result 616.

Figure 7:
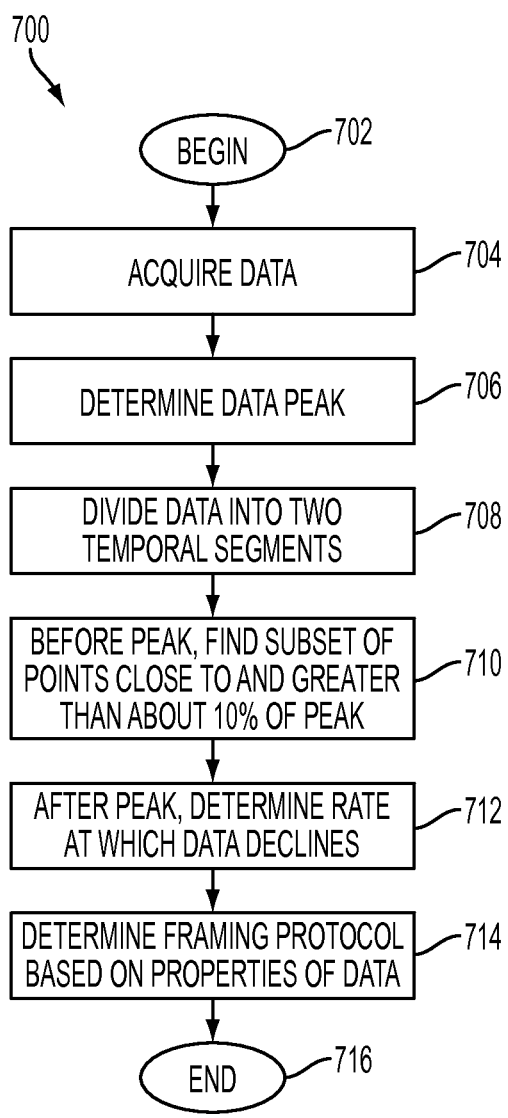
FIG. 7 depicts a diagram of an exemplary method according to a preferred embodiment in accordance with aspects disclosed herein.

FIG. 7 depicts an exemplary method 700 in accordance with embodiments disclosed herein. The method 700 begins at step 702.

After step 702, the method 700 proceeds towards step 704. At step 704, a patient's data is acquired. The patient data may be acquired from memory, transmitted from a remote device, or transmitted towards a processor. The patient data includes the number of radioactive decay events (for both stress and rest) and the times at which the events occurred. After, the acquisition step 704, the method 700 proceeds towards step 706.

At step 706, a peak value (i.e., the highest value) of the acquired patient data is determined. After determination of the peak value, the method 700 proceeds towards step 708.

At step 708, the peak value is used to divide the patient's data into two temporal segments (i.e., one segment including all data before the peak value occurs and the other segment including all data after the peak value occurs). After step 708, the method 700 proceeds towards step 710.

At step 710, the method 700 analyzes the segment which includes the data that occurred before the peak value. A subset of points which are both close to the peak value and greater than 10% of the maximum. The rising slope (i.e., the slope prior to and approaching peak) is calculated (e.g., using linear regression). After step 710, the method 700 proceeds towards step 712.

At step 712, the slope (i.e., a declining slope) after the peak value has occurred is calculated. Although various calculations may be used to determine the slope after the peak value has occurred, illustratively the slope is calculated using Equations (2) and (3) below. The best fit to a decaying exponential can be calculating using Equation (2):

$$f(t) = Ae^{-st} \qquad \text{Equation (2)}$$

where f(t) represents the data, A represents an initial value, e represents the natural base, t is time, and s is a decay parameter that indicates the rate at which the data values declines (i.e., the slope) after the peak.

There are various ways to calculate the decay parameter s. For example, the decay parameter s may be calculated using Equation (3):

$$s = \frac{n \sum_{t_i \geq p}(t_i \ln(f(t_i))) - \sum_{t_i \geq p} t_i \sum_{t_i \geq p} \ln(f(t_i))}{\sum_{t_i \geq p} t_i^2 - \left(\sum_{t_i \geq p} t_i\right)^2} \qquad \text{Equation (3)}$$

where s is the decay parameter (i.e., the slope), t is time, n is the number of data points following the peak value, the summation is taken over $t \geq p$ (where p is the peak value), and f(t) denotes the data. After calculation of the declining slope, the method 700 proceeds towards step 714.

At step 714, a framing protocol is selected based upon the properties of the data. The number of frames and the parameters of the frames (offset in time and frame duration) may change in response to the measured position in time and sharpness in time of the peak in the data. In various embodiments, the framing protocol is selected from a group of framing protocols stored in memory (e.g., stored in a look-up table). In other embodiments, the number of frames, in the framing protocol, and their durations may be calculated. Thereafter the method 700 proceeds towards and ends at step 716.

Although method 700 is described as calculating the rising slope prior to calculating the declining slope that description is not intended in any way to limit the scope of the invention. For example, in various embodiments, the declining slope may be calculated before the rising slope.

Figure 8:
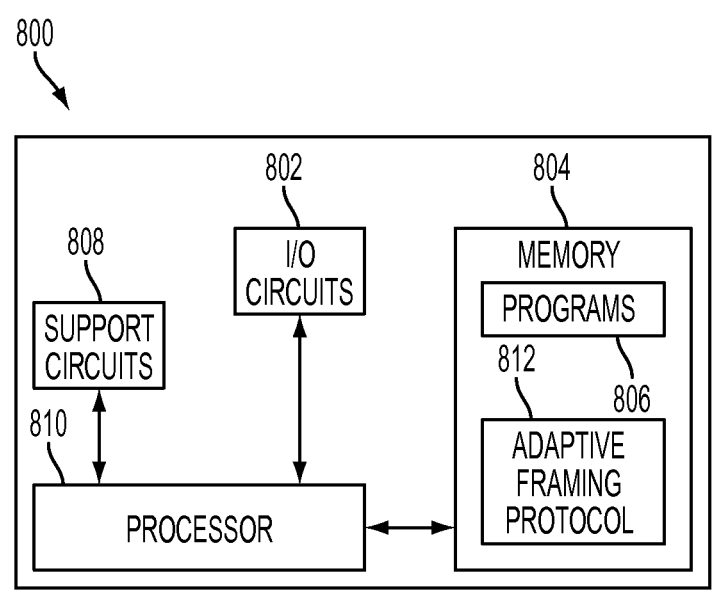
FIG. 8 depicts an embodiment of a high-level block diagram of a computer architecture used in accordance with aspects disclosed herein.

FIG. 8 depicts a high-level block diagram of a general-purpose computer architecture 800 for providing an adaptive framing protocol. For example, the general-purpose computer 800 is suitable for use in performing the method of FIG. 7. The general-purpose computer of FIG. 8 includes a processor 810 as well as a memory 804 for storing control programs and the like. In various embodiments, memory 804 also includes programs (e.g., depicted as an "adaptive framing module" 812 for determination of a framing protocol based on the properties of the data) for performing the embodiments described herein. The processor 810 cooperates with conventional support circuitry 808 such as power supplies, clock circuits, cache memory and the like as well as circuits that assist in executing the software routines 806 stored in the memory 804. As such, it is contemplated that some of the process steps discussed herein as software processes may be loaded from a storage device (e.g., an optical drive, floppy drive, disk drive, etc.) and implemented within the memory 804 and operated by the processor 810. Thus, various steps and methods of the present invention can be stored on a computer readable medium. The general-purpose computer 800 also contains input-output circuitry 802 that forms an interface between the various functional elements communicating with the general-purpose computer 800.

Although FIG. 8 depicts a general-purpose computer 800 that is programmed to perform various control functions in accordance with the present invention, the term computer is not limited to just those integrated circuits referred to in the art as computers, but broadly refers to computers, processors, microcontrollers, microcomputers, programmable logic controllers, application specific integrated circuits, and other programmable circuits, and these terms are used interchangeably herein. In addition, although one general-purpose computer 800 is depicted, that depiction is for brevity on. It is appreciated that each of the methods described herein can be utilized in separate computers.

The invention having been described, it will be apparent to those skilled in the art that the same may be varied in many ways without departing from the spirit and scope of the invention. In particular, while the invention has been described with reference to utilizing Equations (2) and (3), the inventive concept does not depend upon the use of Equations (2) and (3). Any acceptable methods may be used determine the slope before peak value and the slope after peak value. As previously explained adaptive framing may be performed by a programmable computer loaded with a software program, firmware, ASIC chip, DSP chip or hardwired digital circuit. Any and all such modifications are intended to be included within the scope of the following claims.

While the foregoing is directed to embodiments of the present invention, other and further embodiments of the invention may be devised without departing from the basic scope thereof, and the scope thereof is determined by the claims that follow.

The invention claimed is:

1. A method comprising:
   acquiring patient data;
   determining a data peak in list mode;
   dividing said patient data into a first data segment before said data peak and a second data segment after said data peak;
   determining a rising slope and a declining scope from said first and said second data segments;
   arranging the data into a large number of short frames before the peak and arranging the data into a small number of long frames after the peak; and
   determining an adaptive framing protocol from said rising slope and said declining slope,
   wherein patient data changes rapidly before the peak and changes slowly after the peak.

2. The method of claim 1 wherein said patient data is acquired from one of internal memory, a remote device, and transmission towards a processor.

3. The method of claim 1 wherein said patient data comprises a plurality of radioactive decay events and a time stamp associated with each radioactive decay event in said plurality.

4. The method of claim 1 wherein said rising slope is determined using linear regression.

5. The method of claim 1 wherein said declining slope is determined using a decaying exponential equation comprising:

$$f(t)=Ae^{-st}$$

where f(t) represents the data, A represents an initial value, e represents a natural base, t is time, and s is a decay parameter that indicates a rate at which patient data values declines after said peak value.

6. The method of claim 5 wherein s may be calculated using:

$$s = \frac{n\sum_{t_i \geq p}(t_i \ln(f(t_i))) - \sum_{t_i \geq p} t_i \sum_{t_i \geq p} \ln(f(t_i))}{\sum_{t_i \geq p} t_i^2 - \left(\sum_{t_i \geq p} t_i\right)^2}$$

where s is said decay parameter, t is time, n is a number of data points following said perk value, a summation is taken over $t \geq p$ (where p is said perk value), and f(t) denotes said patient data.

7. The method of claim 1 wherein said adaptive framing protocol is selected from a group of framing protocols.

8. The method of claim 1 wherein said determination of said adaptive framing protocol comprises calculating a number of frames and a duration of each frame in said number of frames.

9. The method of claim 1 wherein said adaptive framing protocol is used in medical imaging.

10. A computer-readable medium having stored thereon a plurality of instructions, the plurality of instructions, when executed by a processor, cause the processor to perform the steps comprising of:
    acquiring patient data;
    determining a data peak;
    dividing said patient data into a first data segment before said data peak and a second data segment after said data peak;
    determining a rising slope and a declining scope from said first and said second data segments;
    arranging the data into a large number of short frames before the peak and arranging the data into a small number of long frames after the peak; and
    determining an adaptive framing protocol from said rising slope and said declining slope,
    wherein patient data changes rapidly before the peak and changes slowly after the peak.

11. The computer-readable medium of claim 10 wherein said patient data is acquired from one of internal memory, a remote device, and transmission towards a processor.

12. The computer-readable medium of claim 10 wherein said patient data comprises a plurality of radioactive decay events and a time stamp associates with each radioactive decay event in said plurality.

13. The computer-readable medium of claim 10 wherein said rising slope is determined using linear regression.

14. The computer-readable medium of claim 10 wherein said declining slope is determined using a decaying exponential equation.

15. The computer-readable medium of claim 10 wherein said adaptive framing protocol is selected from a group of 5 framing protocols.

16. The computer-readable medium of claim 10 wherein said determination of said adaptive framing protocol comprises calculating a number of frames and a duration of each frame in said number of frames.

* * * * *